(12) United States Patent
Hermanson et al.

(10) Patent No.: US 8,207,100 B1
(45) Date of Patent: Jun. 26, 2012

(54) SPECIFIC PERFUMES HAVING ENHANCED EFFICACY WHEN USED IN SPECIFIC LIQUID CONCENTRATE COMPOSITIONS

(75) Inventors: Kevin Hermanson, Hamden, CT (US); Lin Yang, Woodbridge, CT (US); Georgia Shafer, Southbury, CT (US); Anat Shiloach, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/070,691

(22) Filed: Mar. 24, 2011

(51) Int. Cl.
*C11D 17/00* (2006.01)
(52) U.S. Cl. .......................... 510/101; 510/156; 510/424
(58) Field of Classification Search .......................... None
See application file for complete search history.

(56) References Cited

U.S. PATENT DOCUMENTS

| | | | |
|---|---|---|---|
| 5,540,853 A * | 7/1996 | Trinh et al. | 510/101 |
| 5,759,969 A | 6/1998 | Tsaur et al. | |
| 5,849,310 A * | 12/1998 | Trinh et al. | 424/401 |
| 7,884,060 B1 | 2/2011 | Hermanson et al. | |
| 7,884,061 B1 | 2/2011 | Hermanson et al. | |
| 2008/0139434 A1 | 6/2008 | Basappa et al. | |
| 2009/0312224 A1 | 12/2009 | Yang et al. | |

FOREIGN PATENT DOCUMENTS

| | | |
|---|---|---|
| WO | 2010/052070 | 5/2010 |
| WO | 2010/052072 A2 | 5/2010 |
| WO | 2010/052073 A1 | 5/2010 |
| WO | 2010/052147 | 5/2010 |
| WO | 2010/052171 | 5/2010 |

OTHER PUBLICATIONS

Co-pending application for Yang et al., U.S. Appl. No. 13/070,699, filed Mar. 24, 2011 for Methods for Enhancing Perfume Efficacy.

* cited by examiner

*Primary Examiner* — Necholus Ogden, Jr.
(74) *Attorney, Agent, or Firm* — Ronald A. Koatz

(57) ABSTRACT

The invention relates to specific synergistic combinations (providing perfume delivery in both diluted and undiluted compositions) between specific soap-based liquid concentrates and particularly defined perfumes. The invention further relates to a method of delivering enhanced smell and/or enhanced fragrance intensity in use using such combinations.

18 Claims, No Drawings

SPECIFIC PERFUMES HAVING ENHANCED EFFICACY WHEN USED IN SPECIFIC LIQUID CONCENTRATE COMPOSITIONS

FIELD OF THE INVENTION

The present invention relates to a specific synergistic combination between specific liquid concentrate liquids (e.g., specific soap-based concentrate having defined rheologies and defined fatty acid to soap criteria) and specifically defined perfumes and/or class of perfumes. More specifically, applicants have found that when such particularly defined perfumes or class of perfume (relative to perfumes broadly) are used in specific liquid concentrate compositions (relative, for example, to use in other compositions), they have far greater perfume efficacy (e.g., can be used in lower amounts to provide the same effect). This effect can be seen, for example, in ability to provide enhanced smell in undiluted liquids (such as found in marketed products when top is opened); or enhanced fragrance intensity in use (e.g., when product is diluted in use).

BACKGROUND

Concentrated liquid compositions are not new.

WO 2010/052072 A2 and WO 2010/052073 A1, both to Unilever, for example, disclose hair formulations which are concentrated shampoo compositions. Use of specific oils is said to ensure the liquid compositions remain in a nematic discotic phase rather than lamellar phase.

WO 2010/052147, WO 2010/052070 and WO 2010/052171, also all to Unilever, relate to hair formulations which cover concentrates made with 25-70% alkali metal ether sulfates made in combination with either polypropylene glycol, short chain diols or an aminosilicone.

U.S. Publication No. 2008/0139434 to Basappa et al. discloses mixtures of alkyl ether sulphate and a cosurfactant at concentration between 50-95%. A manufacturing process for in-line mixing is also disclosed.

None of these references discloses composition comprising specific perfumes in specifically defined soap-based concentrated liquids. All the references relate to concentrated synthetic surfactant based liquids.

Applicants have filed two applications entitled "Concentrated Liquid Soap Formulations Having Readily Pumpable Viscosity" to Hermanson et al., filed Aug. 12, 2009 (U.S. Ser. No. 12/539,770); and "Concentrated Liquid Soap Formulations with Greater than 50% Long Chain Soap and Fatty Acid Having Readily Pumpable Viscosity" to Hermanson et al, also filed Aug. 12, 2009 (U.S. Ser. No. 12/539,776). Both disclose soap-based concentrated liquid compositions. Neither relates to use of a particular class of perfumes resulting in enhanced efficacy of such perfumes when used in specific liquid concentrate compositions.

U.S. Publication No. 2009/0312224 to Yang et al. discloses use of certain classes of perfume in concentrated liquids. The concentrated liquids are synthetic-surfactant based compositions and the benefit of specific perfumes in soap-based concentrated liquids is not recognized or suggested.

BRIEF SUMMARY OF THE INVENTION

Unexpectedly, applicants have now found that if a specific class of perfume is used in specific soap-based (e.g., 40-80% liquid fatty acid and/or soap, wherein liquid soap comprises 50% or more of surfactant system) liquid compositions, a synergistic effect is obtained and perfumes have greater efficacy relative to (1) use of different class of perfume in the same soap-based liquids; or (2) use of same class of perfume in different (e.g., non-concentrate) compositions.

In one embodiment, the present invention relates to liquid fatty acid, soap-based concentrate compositions comprising:
1) 40 to 80%, preferably 50 to 75% by wt. fatty acid and/or soap;
2) 0 to 25%, preferably 1 to 20% by wt., more preferably 2 to 15% by wt. synthetic non-soap surfactant;
3) 10 to 65%, preferably 20 to 65%, more preferably 20 to 60% by wt. solvent which may be combination of water and/or co-solvents preferably selected from alkylene glycol;
4) 0:01 to 3% perfume component haying a polarity >4 $MPa^{1/2}$, preferably >6 $MPa^{1/2}$; wherein perfume component comprises a benzene ring having added, to one position on the ring, a $C_1$ to $C_6$ alkyl group containing a functional group selected from the group. Consisting of alcohol, acetate, aldehyde and mixtures thereof. In one embodiment, the functional group is a terminal alcohol added to the $C_1$ to $C_6$ alkyl group.

Preferably, the concentrates have viscosity of between 10,000 and 100,000 cps measured at 20° C. on a Brookfield Viscometer after two (2) minutes at 10 rpm using Spindle RV7. Further, preferably the ratio of $C_{12}$ to $C_{14}$ chain length in fatty acid/soap should be 0.4:1 to 1.4:1; the ratio of $C_{12}$-$C_{14}$ to $C_{16}$-$C_{18}$ in fatty acid and/or soap should be between 8:1 and 2:1 and ratio of $C_{12}$-$C_{14}$ to $C_{16}$ fatty acid and/or soap should be 30:1 to 2:1. Preferably, there should be some alkali metal lauryl ether sulfate (0 to 25%) and alkoxylation should be between 0.5 and 2.0. Also preferably solvent should be $C_2$ to $C_4$ alkylene glycol (e.g., propylene glycol) of weight average molecular weight between 425 and 3600.

Preferably when criticalities related to concentrate composition and perfumes components are met, when measuring against a soap-based non-concentrate composition comprising 5-25% fatty acid soap and overall (including soap) less than 30% surfactant; (a) the perfume component used has a perfume efficacy coefficient (PEC) greater than 1, preferably >1.1, more preferably >1.2 when such measurement is for undiluted concentrate compositions against undiluted non-concentrates; and (b) the perfume component has a PEC≧2 when such measurement is for diluted concentrate against diluted concentrates (dilution defined as per protocol). PEC (which measures, efficacy of one composition versus another) is defined by the equation:

$$PEC=[PHC_1/(P_1\%/PS_1\%)]/[PHC_2/(P_2\%/PS_2\%)]$$

wherein PHC is perfume headspace concentration as measured by GC (gas chromatography)/FID (flame ionization detector) measurement;

wherein P % is perfume dosage in said equation;

wherein PS % is surfactant level in said equation;

wherein 1 refers to level of concentrate such that $P_1$, for example, is level of perfume in concentrate and $PS_1$ is level of surfactant in concentrate;

wherein 2 refers to level of comparative (e.g., non-concentrate body wash composition in which PHC is comparatively measured) such that $P_2$ is level of perfume in said non-concentrate and $PS_2$ is level of surfactant in said non-concentrate composition.

As indicated, applicants have found quite unexpectedly that defined perfume used in defined concentrate compositions provide better perfume efficacy (defined by PEC greater than 1, with standard deviation, for undiluted versus undiluted composition comparison; and by PEC≧2 for a diluted versus diluted composition comparison). Examples of specific perfumes include phenylethyl alcohol (PEA), and benzyl acetate. In comparing undiluted compositions, enhanced efficacy manifests itself as enhanced smell when opening product containers (e.g., the consumer experiences enhanced smell efficacy), and in comparing diluted versus diluted, it manifests itself in enhanced "bloom" in use (e.g., enhanced smell during wash). Applicants have also noted that enhanced PEC correlates with high polarity, and perfume of defined (e.g., bulky) molecular structure as is seen from claimed perfumes.

Applicants have also noted that some perfume components (e.g., those correlated with high polarity and small molecular size) have PEC about 1, with standard deviation, which offers about parity performance; and some perfume components (e.g., typically non-polar components such as limonene and pinene) exhibit PEC less than 1, or less perfume performance from concentrate compared to non-concentrate.

It is completely unpredictable that only use of specific perfume compounds or class of compounds used in specific soap-based liquid concentrates provides the observed superior perfume efficacy.

In another embodiment, applicants have also identified a class of perfume wherein, when measuring for perfume smell in undiluted compositions relative to undiluted non-concentrates, PEC>1, but when measuring for bloom in diluted concentrate versus diluted non-concentrate, PEC>1 and <2.

In a third embodiment, the invention provides a method of ascertaining which perfume component(s) will provide enhanced perfume efficacy by measuring for PEC, wherein values of PHC, P and PS used to measure for PEC are defined above; and selecting those components which have measured PEC value greater than 1, preferably greater than 1.1, more preferably greater than 1.2 (for undiluted comparisons) and PEC$\geq$2 (for diluted comparisons).

In a fourth embodiment, the invention relates to a method of delivering enhanced fragrance smell or detection by consumers from container comprising undiluted liquid body wash (defined to mean the liquid in the container when sold to consumer) which method comprises formulating specific perfume or class of perfumes into specific soap-based concentrated liquids as defined above.

In a fifth embodiment, the invention relates to a method of delivering enhanced fragrance intensity to consumers from dilute liquid bodywash (diluted in use) by formulating specific perfume or class of perfume into specific soap-based concentrated liquid as defined, above. Fragrance release upon dilution is also known as perfume "bloom":

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental example, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y" it is understood that all ranges combining the different endpoints are also contemplated. Further in specifying the range of concentration, it is noted that any particular upper concentration can be associated with any particular lower concentration. Where the term "comprising" is used in the specification or claims, it is not intended to exclude any terms, steps or features not specifically recited. For the avoidance of doubt, the word "comprising" is intended to mean "including" but not necessarily "consisting of" or "composed of". In other words, the listed steps, options, or alternatives need not be exhaustive. All temperatures are in degrees Celsius (° C.) unless specific otherwise. All measurements are in SI units unless specified otherwise. All documents cited are—in relevant part—incorporated herein by reference.

DETAILED DESCRIPTION OF THE INVENTION

The present invention is directed to the synergistic combination of specifically defined perfume components (e.g., defined by specific structures) and specific compositions (e.g., soap-based liquid concentrates where viscosities of compositions and ratios of fatty acid and/or soap chain lengths are defined) in which the perfumes are used.

More specifically, quite unexpectedly, it has been found that defined perfume components used in defined concentrates results in enhanced perfume smell (e.g., when comparing undiluted concentrate to undiluted non-concentrate products) and/or enhanced perfume aroma in use ("bloom") e.g., when comparing diluted concentrate to undiluted non-concentrate products. In one embodiment for example, when particular perfume components (which applicants have found to correlate with polar, bulky perfume components) are used in particular soap-based liquid concentrates, the measured value of PEC is found to be greater than 1 comparing undiluted concentrate to undiluted non-concentrate compositions; and $\geq$2 comparing diluted concentrate to diluted non-concentrate.

It should be understood that perfume components cannot always be specifically defined but, based on knowledge of components which applicants have noted have certain specific attributes (e.g., structure; polarity), applicants can determine more general structures and attributes which will function. In other words, perfume components having certain defined structures and/or polarity provide enhanced benefits noted.

Specifically, in one embodiment the invention relates to liquid fatty acid soap-based concentrate compositions comprising:
1) 40 to 80%, preferably 50 to 75% by wt. fatty acid and/or soap;
2) 0 to 25% by wt., preferably 1 to 20%, more preferably 2 to 15% by wt. synthetic non-soap surfactant;
3) 10 to 65%, preferably 20 to 65%, more preferably 20 to 60% by wt. solvent which may be combination of water and/or co-solvents preferably selected from alkylene glycol;
4) 0.01 to 3% perfume component having polarity >4 MPa$^{1/2}$, preferably >6 MPa$^{1/2}$; wherein the perfume component comprises a benzene ring having added, to one position on the ring, a $C_1$ to $C_6$ alkyl group containing a functional group selected from the group consisting of alcohol, acetate, aldehyde and mixtures thereof— in one embodiment this functional group is a terminal alcohol added to the $C_1$ to $C_6$ alkyl group.

In addition, preferably the concentrates have a viscosity of between 10,000 and 100,000 cps; as measured at 20° C. on Brookfield or similar viscometer after two (2) minutes at 10 rpm (revolution per minute) using Spindle RV7.

The fatty acid soap may have some degree of unneutralized fatty acid (preferably free fatty acid to soap ratio is between 20:100 to 1:100 on a weight basis, reflecting a typical neutralization of 80-99%) where soap and/or fatty acid is formed from fatty acids of varying chain length. Preferably, the ratio of $C_{12}$ to $C_{14}$ chain length fatty acid/soap should be 0.4:1 to 1.4:1. Further, preferably ratio of $C_{12}$-$C_{14}$ chain length fatty acid/soap to $C_{16}$-$C_{18}$ chain length should be 8:1 to 2:1 (this has been found to provide superior product appearance at low temperature); and preferably ratio of $C_{12}$-$C_{14}$ fatty acid/soap to $C_{16}$ fatty acid/soap should be 30:1 to 2:1.

The non-soap surfactant preferably comprises alkali metal lauryl ether sulfate (e.g., sodium LES) and degree of alkoxylation is preferably 0.5 to 2.0. In preferred embodiments, solvent comprises propylene glycol of MW about 425 to 3600.

Preferably when various criticalities are met, when measuring against a soap-based non-concentrate composition comprising 5 to 25% fatty acid soap and total surfactant (including soap) amount of <30%, (a) the perfume used has a perfume efficacy coefficient (PEC) greater than 1, preferably >1.1, more preferably >1.2, even more preferably >1.5 when measuring undiluted concentrate composition against undiluted non-concentrate; and (b) the perfume used has PEC≧2, preferably greater than 2.2 and more preferably greater than 2.5 when measuring diluted concentrate versus diluted non-concentrate (dilution measured under conditions defined in protocol); and wherein PEC is defined by the equation:

$$PEC=[PHC_1/(P_1\%/PS_1\%)]/[PHC_2/(P_2\%/PS_2\%)]$$

wherein PHC is perfume headspace concentration as measured by GC (gas chromatography)/FID measurement;

wherein P % is perfume dosage in said equation;

wherein PS % is surfactant level in said equation;

wherein 1 refers to level of concentrate such that $P_1$, for example, is level of perfume in concentrate and $PS_1$ is level of surfactant in concentrate;

wherein 2 refers to level of comparative (e.g., non-concentrate body wash composition in which PHC is comparatively measured) such that $P_2$ is level of perfume in said non-concentrate and $PS_2$ is level of surfactant in said non-concentrate composition;

Examples of preferred perfume components meeting structure and polarity criteria noted include phenylethylalcohol, benzyl acetate, benzyl alcohol, methyl benzoate and mixtures thereof.

in a second embodiment of the invention, the concentrated compositions comprise the same components (1), (2) and (3) and perfume component has polarity >4 $MPa^{1/2}$. Using different perfume components, when measuring undiluted concentrate versus undiluted non-concentrate, PEC is >1. However, when measuring diluted concentrate versus diluted non-concentrate, PEC>1, but <2.

Examples of perfume compounds having polarity and structure which have these slightly different PEC criteria include undecanoic lactone, N-amyl salicylate, iso-amyl salicylate, dihydromyrcenol, methyl salicylate, benzylaldehyde and mixtures thereof.

Concentrated compositions of the invention comprise 40 to 80%, preferably 50 to 75% fatty soap and it is also required that soap form 50% or more of the surfactant system.

Preferably there is some free fatty acid present such that free fatty acid to soap ratio is about 20:100 to 1:100 on a weight basis. Typically, a ratio of 20:100 to 1:100 reflects a neutralization (if soap is formed in situ versus combining fatty acid and pre-formed soap) of about 80-99%, preferably 85-99%.

Any counterion may be used although use of potassium counterion is preferred since sodium counterion may raise viscosity above what is suitably preferred. Amine based counterion (e.g., trialkanolamine) may also be used.

It is also preferred that >75%; more preferably 80 to 100% of soaps and fatty acids be saturated.

Further, the ratio of $C_{12}$ to $C_{14}$ chain length fatty acid/soaps is preferably 0.4:1 to 1.4:1. Ratio of $C_{12}$-$C_{14}$ chain length fatty acid/soap to $C_{16}$-$C_{18}$ chain length is preferably 8:1 to 2:1; and ratio of $C_{12}$-$C_{14}$ fatty acid/soap to $C_{16}$ fatty acid/soap is preferably 30:1 to 2:1, more preferably 20:1 to 10:1.

Compositions of the invention should also comprise 0% to 25%, preferably 1% to 20%, more preferably 2% to 15% by wt. synthetic non-soap surfactant.

Typically, synthetic surfactant, if present, will comprise at least one anionic surfactant (e.g., alkyl sulfate). Preferably, the compositions will comprise a combination of anionic synthetic and amphoteric surfactant (e.g., betaine), especially when anionic comprises 50% or greater of such mixture of synthetics.

In a preferred embodiment, amino is alkali metal lauryl ether sulfate (e.g., sodium LES) and preferably, aloxylation is between 0.5 and 2.0.

The concentrate compositions of the invention further comprise 10% to 65%, preferably 20 to 65% by wt. solvent. The solvent comprises water or caustic neutralizing solution and may further comprise non-water co-solvent, e.g., polypropylene glycol.

Generally, the greater the amount of co-solvent, the less water required. It is also easy to keep viscosity within preferred range as more co-solvent and less water is used.

Viscosity reducing co-solvents of the invention include propylene glycol, dipropylene glycol, polypropylene glycol, ethylene glycol, polyethylene glycol and many other such related solvents as would be well known to those skilled in the art.

In one embodiment, glycerin can be used as co-solvent. While glycerin does not enhance low temperature stability, low viscosity product can be made with small amounts of glycerin. At levels above about 10%, higher amounts of co-solvent and/or synthetic surfactant might have to be used.

In a preferred embodiment, solvent comprises polypropylene glycol of weight average MW about 425 to about 3600.

The concentrate formulations of the invention, in addition to comprising soap/fatty acid, solvent and synthetic surfactant, may also comprise various benefit agents and/or other ingredients which can typically be used in flowable, liquid personal care formulations.

Benefit agent may be any material that has potential to provide an effect on, for example, the skin.

The benefit agent may be water insoluble material that can protect, moisturize or condition the skin upon deposition from compositions of invention. These may include silicon oils and gums, fats and oils, waxes, hydrocarbons (e.g., petrolatum), higher fatty acids and esters, vitamins, sunscreens. They may include any of the agents; for example, mentioned at column 8, line 31 to column 9, line 13 of U.S. Pat. No. 5,759,969, hereby incorporated by reference into the subject application.

The benefit agent may also be a water soluble material such as glycerin, polyols (e.g., saccharides), enzyme and α- or β-hydroxy acid either alone or entrapped in an oily benefit agent.

The compositions may also comprise perfumes, sequestering agents such as EDTA or EHDP in amounts 0.01 to 1%, preferably 0.01 to 0.05%; coloring agents, opacifiers and pearlizers such as zinc stearate, magnesium stearate, $TiO_2$, mica, EGMS (ethylene glycol monostearate) or styrene/acrylate copolymers.

The compositions may further comprise antimicrobials such as 2-hydroxy 4,2'4'trichlorodiphenylether (DP300), 3,4, 4'-trichlorocarbanilide, essential oils and preservatives such as dimethyl hydantoin (Glydant XL 1000), parabens, sorbic acid, etc.

The compositions may also comprise coconut acyl mono or diethanol amides as suds boosters, and strongly ionizing salts such as sodium chloride and sodium sulfate may also be used to advantage.

Antioxidants such as, for example, butylated hydroxyl toluene (BHT) may be used advantageously in amounts of about 0.01% or higher if appropriate.

Cationic conditioner which may be used including Quatrisoft LM-200 Polyquaternium-24, Merquat Plus 3330-Polyquaternium 39; and Jaguar® type conditioners.

Composition may also include clays such as Bentonite® clays as well as particulates such as abrasives, glitter, and shimmer.

Non-concentrate soap-based composition (against which concentrated compositions may be compared when PEC measurements are made) typically comprise 10-30%, preferably 15-25% soap fatty acid soap.

Finally, the compositions of the invention comprise specific class of perfume components which, having polarity >4 $MPa^{1/2}$, preferably >6 $MPa^{1/2}$ and structures as defined.

In another embodiment of the invention, the invention relates to a method of delivering enhanced fragrance smell or detection by consumers from container comprising undiluted liquid body wash (defined to mean the liquid in the container when sold to consumer) which method comprises formulating specific perfume or class of perfumes as defined into soap-based concentrated liquids as also defined above.

In yet another embodiment, the invention relates to a method of delivering enhanced fragrance intensity to consumers from dilute liquid bodywash (diluted in use) by formulating specific perfume or class perfume as defined into soap-based concentrated liquid as defined above.

EXAMPLES

Protocol

The impact of soap/syndet body wash concentration on fragrance performance was measured by evaluating two key fragrance attributes of a regular body wash base and a body wash concentrate. The composition of the concentrated body wash is shown in Table I and the composition of the regular body wash is shown in Table II. Both the concentrated and the regular body wash are soap/syndet body washes. The concentrated body wash base has an active level (soap, fatty acid and syndet detergent) which is approximately three times higher than the regular body wash.

The first attribute measured is the concentration of fragrance in the static headspace above an undiluted (neat) sample of either the concentrate or regular (non-concentrate) body wash. This measurement evaluates the amount of fragrance that a consumer smells when they sniff the fragrance from a bottle. This measurement is sometimes referred to as the initial impact assessment. In this measurement, 2 grams of a fragranced body wash is sealed in a 20 ml GC (gas chromatography) vial. The air above the body wash is allowed to come to equilibrium with the body wash sample by leaving the sealed GC vial in room temperature for at least 72 hours. After equilibrium is achieved, the relative fragrance concentration in the air of the GC vial is measured by GC/FID (gas chromatography/flame ion detector). Triplicate GC samples were made and measured for each body wash.

The second attribute measured was the amount of fragrance in the static headspace above a diluted sample. The fragrance concentration above the diluted body wash correlates well with the fragrance intensity that a consumer experiences during a shower when using the body wash product. For this measurement, the regular body wash was diluted 10 times and the concentrated body wash was diluted 30 times with water. Because consumers use ⅓ the amount of the 3× concentrated body wash compared to the regular body wash, the in-use dilution factor of the concentrated body wash is three times higher. Again, 2 gram of the diluted body wash is sealed in a 20 ml GC vial. The air above the diluted body wash is allowed to come to equilibrium with the body wash sample by leaving the sealed GC vial in room temperature for at least 24 hours. After equilibrium is achieved, the relative fragrance concentration in the air of the GC vial is measured by GC/FID (gas chromatography/flame ion detector). Triplicate GC samples were made and measured for each diluted body wash.

For measurement of both attributes, GC (e.g., column used was HP-5MS column from Agilent) conditions were as follows: Injector was in splitless mode using helium as carrier gas. Injection port was heated to about 250° C. and flow was purged to split vent 50 ml/min at zero minutes. Column was in constant flow mode with 1.3 ml/min flow rate. Oven temperature ramp: hold at 75° C. for 2 minutes, then increase oven temperature at a rate of 6° C./min to 100° C., 1.5° C./min to 150° C., 3° C./min to 190° C., 30° C./min to 300° C. and hold for 2 minutes. Autosampler's conditions were: No incubation (all experiments done in room temperature). SPME (solid phase micro-extraction) fiber was inserted into the sample headspace for a 5 minute extraction and then injected to the injector for a 15 minute desorption.

Example 1

A 3× concentrate formulation with water concentration between 27 and 30% is described in TABLE I below. In this concentrate formulation the ratio of $C_{12}$ to $C_{14}$ chain length fatty acid and/or soap is 1.0; the ratio of $C_{12}$-$C_{14}$ to $C_{16}$-$C_{18}$ fatty acid and/or soap is 5.2 and the ratio of $C_{12}$-$C_{14}$ to $C_{16}$ fatty acid and/or soap is 10. A regular body wash formulation with water concentration of 76% is also described in TABLE II below as comparative. Potassium soap was used in both body washes.

TABLE I (Concentrated Body Wash)

|  | % in product as 100% active |
|---|---|
| Fatty Acid and Potassium Soap | 59.5% |
| Sodium Laureth Sulfate | 6.5% |
| Cocamidopropyl Betaine | 2.3% |
| Water | 28.3% |
| Preservative | 0.3% |
| Polypropylene Glycol | 3.1% |

TABLE II (Regular Body Wash)

|  | % in product as 100% active |
|---|---|
| Fatty Acid Soap | 17.0% |
| Sodium Laureth Sulfate | 2.1% |
| Cocamidopropyl Betaine | 0.7% |
| Water | 75.8% |
| Preservative | 0.3% |
| KCl | 2.5% |
| Methylcellulose | 0.5% |
| Optical Modifiers | 1.0% |

Because the active level is higher, consumers will use a lower dose of the concentrated body wash than the regular body wash. In order for consumers to dose the same amount of fragrance from both the concentrate and regular body washes, the fragrance level needs to be increased in the concentrated body wash by maintaining the same ratio of fragrance to active surfactant. In the subject invention, it has been unexpectedly found that at equal fragrance to surfactant ratios some perfume compounds perform better in a concentrated body wash than in a regular body wash under both neat and dilute evaluations. There is no obvious reason for this behavior.

To assess the performance of different fragrance compounds in concentrated soap/syndet body washes, a perfume oil (Lalingwin) which contains eight different compounds of various physico-chemical properties was used in the evaluation. The composition of Lalingwin fragrance is shown in TABLE III. This fragrance oil was evaluated at two different concentrations in the concentrated body wash (2% and 3% fragrance) and compared to the regular body wash containing 1% fragrance.

TABLE III

Composition of Lalingwin fragrance

| Ingredient | CAS | Wt. % |
|---|---|---|
| Beta pinene | 127-91-3 | 2.5 |
| Hexyl acetate | 142-92-7 | 1.2 |
| Limonene | 138-86-3 | 1.8 |
| Dihydromyrcenol | 53219-21-9 | 12.0 |
| Phenyl ethyl alcohol (PEA) | 60-12-8 | 12.0 |
| Benzyl acetate | 140-11-4 | 12.0 |
| Citronellol | 106-22-9 | 21.5 |
| Lilial | 80-54-6 | 37.0 |

The perfume efficiency, reflecting perfume impact per unit weight of product, was determined by defining a perfume efficacy coefficient. Because the amount of the concentrated body wash which is used by consumers is proportional to the amount of surfactant in the body wash, e.g., consumer use less concentrated product compared to a regular body wash, the perfume efficacy coefficient (PEC) is defined as a measure of the cost efficacy of perfume per dose. The PEC is given by the expression:

$$PEC = [PHC_1/(P_1\%/PS_1\%)]/[PHC_2/(P_2\%/PS_2\%)] \quad \text{equation 1}$$

where PHC is perfume headspace concentration as measured by GC/FID (GC/FID measurement method is described in Protocol); P % is perfume dosage in said format; PS % is surfactant level in said format. 1, in this case, refers to concentrated format; 2, the "regular" body wash format. In all the examples below, the concentrate composition listed in TABLE I was used as the concentrate format with 68.3% of surfactant level (e.g., $PS_1\% = 68.3\%$). The "regular" body wash formation (composition listed in TABLE II) has surfactant level of 19.8% (e.g., $PS_2\% = 19.8\%$).

In short the PEC illustrates the perfume oil performance. When comparing concentrated body washes to regular body washes the PEC is the proper way to assess perfume performance because consumers dose a concentrated body wash according to the surfactant level. Because consumers dose according to surfactant level, in order for consumers to dose the same amount of perfume in the concentrated and regular body washes, the perfume to surfactant ratio must be the same. The perfume oils with the highest PEC values provide the largest impact from a concentrated body wash relative to a regular body wash. For perfume oils with a PEC>1 the perfume oil will perform better in the concentrated body wash than in the regular body wash. For a PEC<1 the perfume oil will perform worse in the concentrated body wash than in the regular body wash.

Example 2

Table IV shows the PEC of various perfume compounds in the concentrated body wash (Table I) using 2% of Lalingwin perfume oil (TABLE III), compared to the regular body wash (TABLE II). Perfume release from the neat undiluted product was measured using GC/FID to obtain readings of PHC (perfume headspace concentration) for both concentrate and "regular" body wash format. PEC (perfume efficacy coefficient) for each Lalingwin ingredient in the concentrate relative to the "regular" body wash format was thus calculated using equation 1.

TABLE IV

|  | Concentrate body wash, 2% Lalingwin | |
|---|---|---|
| chemical name | PEC | Stdev |
| beta pinene | 0.86 | 0.02 |
| hexyl acetate | 0.94 | 0.06 |
| limonene | 0.61 | 0.02 |
| dihydromyrcenol | 1.20 | 0.09 |
| PEA | 2.73 | 0.90 |
| Benzyl acetate | 1.55 | 0.22 |
| citronellol | 0.88 | 0.09 |
| filial | 0.97 | 0.08 |

From Table IV, it was found unexpectedly that the concentrate format provides better performance (PEC>1 with STDEV) in perfume release from neat product for compounds such as dihydromyrcenol, PEA and Benzyl acetate. These compounds are similar in that they all have a high polarity (e.g., polarity >4 $MPa^{1/2}$) and a bulky molecular structure. It was also found that the concentrate format provides parity perfume performance (PEC≈1 with STDEV) in perfume release from neat product for compounds of relatively high polarity and small in molecular size, such as hexyl acetate. For non-polar compounds such as limonene and pinene, concentrate format exhibits less perfume performance (PEC<1 with STDEV) in perfume release from neat product.

Example 3

Table V shows the PEC of the concentrated body wash (TABLE I) with 3% of Lalingwin perfume oil (TABLE III) compared to the regular body wash (Table II) with 1% of Lalingwin perfume oil. Perfume release from neat product was measured using GC/FID to obtain readings of PHC (perfume headspace concentration) for both concentrate and "regular" body wash format. PEC (perfume efficacy coefficient) of each Lalingwin ingredient in the concentrate relative to the "regular" body wash, format was thus calculated using equation 1.

TABLE V

| chemical name | Concentrate body wash, 3% Lalingwin | |
|---|---|---|
| | PEC | stdev |
| beta pinene | 0.79 | 0.02 |
| hexyl acetate | 0.96 | 0.05 |
| limonene | 0.60 | 0.01 |
| dihydromyrcenol | 1.12 | 0.05 |
| PEA | 2.40 | 0:21 |
| Benzyl acetate | 1.52 | 0.03 |
| Citronellol | 0.83 | 0.03 |

Again, from Table V, it was found unexpectedly that concentrate format provides better performance (PEC>1 with STDEV) in perfume release from compounds which have a relatively high polarity and a bulky structure such as dihydromyrcenol, PEA and Benzyl acetate. It was also found that concentrate format provides parity perfume performance (PEC≈1 with STDEV) in perfume release from neat product for compounds of relatively high polarity and small in molecular size, such as hexyl acetate. For non-polar compounds such as limonene and pinene, the concentrate format exhibits less perfume performance (PEC<1 with STDEV) in perfume release from neat product.

The similarity in PEC values between a 2% fragrance dose and a 3% fragrance dose (Table IV and V) is a direct result of Henry's law which states that the equilibrium perfume concentration in the gas headspace will scale linearly with the perfume concentration in the liquid. The fact that the fragrance compounds obey Henry's law shows that the PEC values are intrinsic to each of the perfume oils and it does not matter at what fragrance level the PEC values are measured.

The results in Example III show that if a fragrance is made using dihydromyrcenol, PEA and Benzyl acetate (compounds with PEC>1) and the concentration of fragrance in a body wash is scaled with the surfactant concentration, this fragrance will have a greater impact in a concentrated body wash than in a normal (unconcentrated) body wash.

Example 4

To understand the in use perfume impact (otherwise known as blooming), 2% of Lalingwin perfume oil (composition listed in TABLE III) was mixed into concentrate (composition listed in TABLE I), and 1% of Lalingwin perfume oil was mixed in "regular" body wash format (composition listed in TABLE II). Perfume release from diluted product was measured using GC/FID to obtain readings of PHC (perfume headspace concentration) for both concentrate and "regular" body wash format. Perfume release from diluted product represents perfume bloom in use during shower and is an important attribute to consumer satisfaction of overall perfume performance of a body wash product. As stated in earlier examples, the amount of body wash that consumers dose during use is approximately in proportion to the overall surfactant level in the body wash formulation. In "regular" body wash product, typically a dilution factor of 10 was used, calculated by amount of product dose vs. amount of water on wetted body. As the concentrate format such as those listed in Table I has approximately three times more surfactant and thus about ⅓ of product dose, a dilution factor of 30 was used for concentrate format in this test.

PEC (perfume efficacy coefficient) of each Lalingwin ingredient in the concentrate (30 times diluted with water) relative to the "regular" body wash format (10 times diluted with water) was thus calculated using equation 1, as an evaluation of perfume performance during product use. The results are listed in TABLE VI.

TABLE VI

| chemical name | Concentrate body wash, 2% lalingwin (30x diluted) | |
|---|---|---|
| | PEC | Stdev |
| beta pinene | 1.49 | 0.09 |
| hexyl acetate | 1.47 | 0.20 |
| limonene | 1.52 | 0.14 |
| dihydromyrcenol | 1.45 | 0.23 |
| PEA | 2.53 | 0.26 |
| Benzyl acetate | 3.62 | 0.55 |
| citronellol | 1.50 | 0.22 |
| Lilial | 1.89 | 0.30 |

Unexpectedly, it was found that after dilution the concentrate format provides better performance (PEC>1 with stdev) in perfume release from diluted product for all the compounds in the Lalingwin perfume oil. Similar to the neat product evaluation (Table IV and V) the compounds with relatively high polarity and a bulky in molecular structure, such, as PEA and Benzyl acetate, demonstrated unusually high perfume release during dilution in the concentrated product (PEC>2 with stdev).

Example 5

3% of Lalingwin perfume oil (composition listed in TABLE III) was mixed into the concentrate format (composition listed in TABLE I), and 1% of Lalingwin perfume oil was mixed in the "regular" body wash format (composition listed in TABLE II). Perfume release from diluted product (30 times dilution for concentrate, 10 times for "regular" format) was measured using GC/FID to obtain readings of PHC (perfume headspace concentration)

PEC (perfume efficacy coefficient) of each Lalingwin ingredient in the concentrate (30 times diluted with water) relative to the "regular" body wash format (10 times diluted with water) was thus calculated, using equation 1, as an evaluation of perfume performance during product use. The results are listed in TABLE VII.

TABLE VII

| chemical name | Concentrate body wash, 3% lalingwin (30x diluted) | |
|---|---|---|
| | PEC | Stdev |
| beta pinene | 1.28 | 0.09 |
| hexyl acetate | 1.56 | 0.23 |
| limonene | 1.50 | 0.16 |
| dihydromyrcenol | 1.55 | 0.26 |
| PEA | 2.65 | 0.22 |
| Benzyl acetate | 4.00 | 0.58 |
| citronellol | 1.63 | 0.25 |
| lilial | 2.01 | 0.33 |

Again, unexpectedly, it was found that, at their diluted stages, the concentrate format provides better performance (PEC>1 with stdev) in perfume release from diluted product for all the compounds in Lalingwin perfume oils. Especially for compounds of relatively high polarity and bulky in molecular structure, such as PEA and Benzyl acetate, significantly higher perfume release from diluted stage (PEC>2 with stdev) was observed with the concentrated format. Note that these two compounds also exhibit superior performance for perfume release from neat product (Table IV and V).

Example 6

The inventors tested more perfume compounds in both concentrate body wash and in regular body wash with similar chemical structure to benzyl acetate (BA) and phenyl ethyl alcohol (PEA), e.g., the two compounds that showed the highest PEC amongst the compounds tested (TABLE IV to VII). The additional compounds tested are: benzyl alcohol, iso-amyl salicylate, N-amyl salicylate, undecanoic lactone, methyl salicylate, benzaldehyde and methyl benzoate. Similar to benzyl acetate and phenyl ethyl alcohol, those compounds have a ring structure containing a polar functional group (Table X and XI).

Each fragrance compound was mixed into the concentrate format (composition listed in TABLE I) at a 0.36% level, and mixed into "regular" body wash format (composition listed in TABLE II) at a 0.12% level. Perfume release from neat product was measured using GC/FID to obtain readings of PHC (perfume headspace concentration). PEC (Perfume efficacy coefficient) of those compounds tested in the neat concentrate format is listed in TABLE VIII.

TABLE VIII

| chemical name | Concentrated body wash, 0.36% of single compound | |
|---|---|---|
| | PEC | Stdev |
| Undecanoic lactone | 1.76 | 0.24 |
| Benzyl alcohol | 1.92 | 0.15 |
| Iso-amyl salicylate | 1.47 | 0.10 |
| N-amyl salicylate | 1.36 | 0.06 |
| Methyl salicylate | 1.23 | 0.12 |
| Benzaldehyde | 1.25 | 0.02 |
| Methyl benzoate | 1.82 | 0.36 |

Example 7

Each fragrance compound listed in Table VIII was mixed into the concentrate format (composition listed in TABLE I) at a 0.36% level, and into the "regular" body wash format (composition listed in TABLE II) at a 0.12% level. Perfume release from the diluted product (30 times dilution for concentrate, 10 times for "regular" format) was measured using GC/FID to obtain readings of PHC (perfume headspace concentration). PEC (Perfume efficacy coefficient) of those compounds from diluted concentrate format was listed in TABLE IX.

TABLE IX

| chemical name | Concentrated body wash, 0.36% of single compound (30× diluted) | |
|---|---|---|
| | PEC | Stdev |
| Undecanoic lactone | 1.67 | 0.35 |
| Benzyl alcohol | 2.27 | 0.08 |
| Iso-amyl salicylate | 1.74 | 0.27 |
| N-amyl salicylate | 1.67 | 0.26 |
| Methyl salicylate | 1.28 | 0.15 |
| Benzaldehyde | 1.40 | 0.13 |
| Methyl benzoate | 1.96 | 0.10 |

Example 8

While not wish to be bound by theory, it was observed from the above examples (EXAMPLE 2-7), that specific structural classes of fragrance compounds are unexpectedly very efficient when used in a concentrated soap/syndet body wash. These fragrance compounds were demonstrated to be efficient under conditions which simulate the initial consumer fragrance evaluation (i.e. smelling from a bottle) and conditions which simulate consumer in-shower fragrance evaluation.

TABLE X lists polarity, molecular structure and PECs (which shows efficacy) of the three best performing fragrance compounds (phenethyl alcohol, benzyl acetate, benzyl alcohol and methyl benzoate). These fragrance compounds have a PEC>1 when evaluated under neat conditions and a PEC when evaluated under dilute conditions. All of these compounds have a very similar molecular structure and a high polarity. Structurally, these three compounds contain a benzene ring which is attached to a single functional group (e.g., alcohol or acetate). These compounds also have a relatively high polarity (polarity >4 $MPa^{1/2}$).

Polarity of perfume compounds are calculated by commercially available software, Molecular Modelling Pro (MMP) software, from ChemSW® (420-F Executive Court North, Fairfield, Calif. 94585). MMP software from ChemSW® is designed to do structure-property analysis by integration of computational chemistry and statistics programs.

TABLE X compounds that are best performers (PEC > 1 as neat; PEC > 2 as diluted): Polarity > 4 $MPa^{1/2}$ with a benzene structure attached to one functional group (e.g., alcohol, acetate, aldehyde)

| | Phenethyl alcohol | Benzyl acetate | Benzyl alcohol | Methyl Benzoate |
|---|---|---|---|---|
| CAS | 60-12-8 | 140-11-4 | 100-51-6 | 93-58-3 |
| Polarity ($MPa^{1/2}$) | 4.25 | 4.32 | 6.29 | 9.78 |
| PEC as neat of concentrate format | >1 | >1 | >1 | >1 |
| PEC as diluted in concentrate format | >2 | >2 | >2 | ≅2 |

TABLE X-continued compounds that are best performers (PEC > 1 as neat; PEC > 2 as diluted): Polarity > 4 MPa$^{1/2}$ with a benzene structure attached to one functional group (e.g., alcohol, acetate, aldehyde)

| | Phenethyl alcohol | Benzyl acetate | Benzyl alcohol | Methyl Benzoate |
|---|---|---|---|---|
| Structure | (structure) | (structure) | (structure) | (structure) |

Table XI lists other fragrance compounds which were also found to perform well in concentrated soap/syndet body washes, but contain greater structural differences than those listed in Table X. These fragrance compounds have a PEC>1 when evaluated under neat conditions and a 1<PEC<2 when evaluated under dilute conditions. In general these compounds have a high polarity.

TABLE XI compounds that are secondary best performers (PEC > 1 as neat; 1 < PEC < 2 as diluted): Polarity > 4 MPa$^{1/2}$ with other chemical structure

| | Undecanoic lactone | N-Amyl salicylate | Iso-Amyl salicylate |
|---|---|---|---|
| CAS | 710-04-2 | 2050-08-0 | 87-20-7 |
| Polarity (MPa$^{1/2}$) | 6.51 | 10.76 | 10.76 |
| PEC as neat of concentrate format | >1 | >1 | >1 |
| PEC as diluted in concentrate format | 1 < PEC < 2 | 1 < PEC < 2 | 1 < PEC < 2 |
| Structure | (structure) | (structure) | (structure) |

| | Dihydromyrcenol | Methyl Salicylate | Benzaldehyde |
|---|---|---|---|
| CAS | 53219-21-9 | 119-36-8 | 100-52-7 |
| Polarity (MPa$^{1/2}$) | 4.23 | 10.76 | 7.38 |
| PEC as neat of concentrate format | >1 | >1 | >1 |
| PEC as diluted in concentrate format | 1 < PEC < 2 | 1 < PEC < 2 | 1 < PEC < 2 |
| Structure | (structure) | (structure) | (structure) |

In comparison, TABLE XI lists compounds which do not result in better fragrance performance when used in a concentrated soap/syndet body wash. These compounds have a PEC under neat conditions which is close to or less than 1. These compounds have a relatively low polarity and are structurally dissimilar to the compounds shown in Table X and XI.

TABLE XII

Compounds that are least performers (PEC < 1 as neat, and 1 < PEC < 2 as diluted): Polarity < 4 MPa$^{1/2}$

| | Citronellol | Lilial | Beta pinene |
|---|---|---|---|
| CAS | 106-22-9 | 80-54-6 | 127-91-3 |
| Polarity (MPa$^{1/2}$) | 2.90 | 2.27 | 0.79 |
| PEC as neat of concentrate format | <1 | ≅1 | <1 |
| PEC as diluted in concentrate format | 1 < PEC < 2 | ≅2 | 1 < PEC < 2 |
| Structure | (structure) | (structure) | (structure) |

| | Hexyl acetate | Limonene |
|---|---|---|
| CAS | 142-92-7 | 5989-27-5 |
| Polarity (MPa$^{1/2}$) | 2.9 | 0.98 |
| PEC as neat of concentrate format | ≅1 | <1 |
| PEC as diluted in concentrate format | 1 < PEC < 2 | 1 < PEC < 2 |
| Structure | (structure) | (structure) |

The results in shown Examples 2-7 have identified seven fragrance compounds which are unexpectedly efficient (PEC>1 under both neat and dilute conditions) when used in a concentrated soap/syndet body wash. These compounds are phenethyl alcohol, benzyl acetate, benzyl alcohol, undecanoic lactone, N-amyl salicylate, Iso-amyl salicylate, dihydromyrcenol, methyl salicylate, benzaldehyde and methyl benzoate. Because fragrance compound efficiency is determined by molecular structure and compound polarity, other compounds with similar structures and polarities are also efficient. This was demonstrated by comparing the compounds shown in Table X. These four compounds (phenethyl alcohol, benzyl acetate, benzyl alcohol and methyl benzoate) are polar molecules made from a benzene ring with a single polar functional group (e.g., alcohol, acetate, or aldehyde). This class of compounds is unexpectedly efficient when used in a soap/syndet concentrated body wash.

Standard Deviation (STDEV) of Perfume Efficiency Values

The headspace above Sample 1 and Sample 2 were measured three times each in order to determine the standard deviation of the headspace measurement. The PEC standard deviation was calculated using these independently measured standard deviations and the law of propagation of error. The law of propagation of error is a standard method as known, for example, from Mandel J. (1964), *The Statistical Analysis of Experimental Data*, New York, N.Y., John Wiley & Sons.

What is claimed is:

1. Liquid fatty acid soap-based concentrate composition comprising:
   1) 40 to 80% by wt. fatty acid and/or soap;
   2) 0 to 25% by wt. synthetic non-soap surfactant;
   3) 10 to 65% by wt. solvent which may be combination of water and/or co-solvents;
   4) 0.01 to 3.0% perfume component with a polarity greater than 4 MPa½;
   wherein said perfume component comprises a benzene ring having attached, to one position on the ring, a $C_1$-$C_6$ alkyl group containing a functional group selected from the group consisting of alcohol, acetate, aldehyde and mixtures thereof;
   wherein concentrate has a viscosity of between 10,000 and 100,000 cps, as measured at 20° C. in Brookfield Viscometer after two (2) minutes at 10 rpm using Spindle RV7;
   wherein, when criticalities of perfume and soap-based concentrates are met, when measuring against a non-concentrate liquid soap-based composition comprising 10-30% fatty acid soap and less than 30% total surfactant, said concentrate has a perfume efficiency coefficient (PEC as defined) of >1, measuring undiluted concentrate versus undiluted non-concentrate; and a PEC≧2, measuring diluted concentrate versus diluted non-concentrate.

2. A composition according to claim 1 wherein the functional group on the perfume is alcohol and said alcohol is a terminal alcohol attached to the $C_1$-$C_6$ alkyl group.

3. A composition according to claim 1 wherein said perfume component is selected from the group consisting of phenethyl alcohol, benzyl acetate, benzyl alcohol, methyl benzoate, and mixtures thereof.

4. A composition according to claim 1 wherein fatty acid is neutralized about 80-99%.

5. A composition according to claim 1 wherein ratio of $C_{12}$ to $C_{14}$ chain length fatty acid and/or soap is 0.4:1 to 1.4:1.

6. A composition according to claim 1 wherein ratio of $C_{12}$-$C_{14}$ chain length fatty acid and/or soap to $C_{16}$-$C_{18}$ chain length is 8:1 to 2:1.

7. A composition according to claim 1 wherein concentrate comprises 50 to 75% fatty acid soap.

8. A composition according to claim 1 where concentrate comprises 1 to 20% synthetic non-soap surfactant.

9. A composition according to claim 6 where concentrate comprises 2 to 15% synthetic non-soap surfactant.

10. A composition according to claim 1 wherein solvent comprises polypropylene glycol.

11. A liquid soap-based concentrate composition comprising:
1) 40 to 80% by wt. fatty acid and/or soap;
2) 0 to 25% by wt. synthetic non-soap surfactant;
3) 10 to 65% by wt. solvent which may be combination of water and/or co-solvents preferably selected from alkylene glycol;
4) 0.01 to 3.0% perfume component with a polarity greater than 4 MPa$^{1/2}$; wherein said compound is selected from the group consisting of dihydromyrcenol, methyl salicylate, benzoaldehyde and mixtures thereof;

wherein concentrate has a viscosity of between 10,000 and 100,000 cps, as measured at 20° C. in Brookfield Viscometer after two (2) minutes at 10 rpm using Spindle RV7; and wherein when criticalities of perfume and soap-based concentrates are met, when measuring against a non-concentrate liquid soap-based composition comprising 10-30% fatty acid soap and less than 30% total surfactant; said concentrate has a PEC value of >1 measuring undiluted concentrate to undiluted non-concentrate, and a PEC defined as 1<PEC<2, measuring diluted concentrate versus diluted non-concentrate.

12. A composition according to claim 11 wherein fatty acid is neutralized about 80-99%.

13. A composition according to claim 11 wherein ratio of $C_{12}$ to $C_{14}$ chain length fatty acid and/or soap is 0.4:1 to 1.4:1.

14. A composition according to claim 11 wherein ratio of $C_{12}$-$C_{14}$ chain length fatty acid and/or soap to $C_{16}$-$C_{18}$ chain length is 8:1 to 2:1.

15. A composition according to claim 11 wherein concentrated comprises 50-75% fatty acid soap.

16. A composition according to claim 11 where concentrate comprises 1 to 20% synthetic non-soap surfactant.

17. A composition according to claim 16 where concentrate comprises 2 to 15% synthetic non-soap surfactant.

18. A composition according to claim 11 wherein solvent comprises polypropylene glycol.

* * * * *